(12) United States Patent
Gann et al.

(10) Patent No.: US 9,233,029 B2
(45) Date of Patent: Jan. 12, 2016

(54) NESTING TAMPON APPLICATOR

(75) Inventors: Diana Lynn Gann, Lebanon, OH (US); Margaret Henderson Hasse, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1659 days.

(21) Appl. No.: 12/488,768

(22) Filed: Jun. 22, 2009

(65) Prior Publication Data

US 2010/0324468 A1  Dec. 23, 2010

(51) Int. Cl.
*A61F 13/32* (2006.01)
*A61F 13/30* (2006.01)
*A61F 13/26* (2006.01)

(52) U.S. Cl.
CPC .................................. *A61F 13/266* (2013.01)

(58) Field of Classification Search
USPC ....................................................... 604/11–18
See application file for complete search history.

(56) References Cited

U.S. PATENT DOCUMENTS

| | | | |
|---|---|---|---|
| 4,276,881 A * | 7/1981 | Lilaonitkul | 604/14 |
| 4,286,595 A * | 9/1981 | Ring | 604/16 |
| 4,536,178 A | 8/1985 | Lichstein et al. | |
| 5,437,628 A | 8/1995 | Fox et al. | |
| 5,453,085 A | 9/1995 | Schoelling | |
| 6,432,076 B1 * | 8/2002 | Wada et al. | 604/15 |
| 6,450,986 B1 | 9/2002 | Binner et al. | |
| 6,508,780 B1 * | 1/2003 | Edgett et al. | 604/15 |
| 6,890,324 B1 | 5/2005 | Jackson et al. | |
| 7,044,928 B2 | 5/2006 | LeMay et al. | |
| 7,338,462 B2 | 3/2008 | Minoguchi et al. | |
| 7,727,208 B2 | 6/2010 | Lemay et al. | |
| 2004/0054317 A1 * | 3/2004 | Lemay et al. | 604/15 |
| 2005/0273038 A1 | 12/2005 | Osborn, III et al. | |
| 2005/0273041 A1 | 12/2005 | Osborn, III et al. | |
| 2006/0155240 A1 | 7/2006 | Osborn, III et al. | |
| 2006/0173400 A1 * | 8/2006 | Suga et al. | 604/18 |
| 2010/0204636 A1 | 8/2010 | Lemay et al. | |

OTHER PUBLICATIONS

PCT International Search Report dated Aug. 12, 2010.

* cited by examiner

*Primary Examiner* — Susan Su
(74) *Attorney, Agent, or Firm* — Andrew J. Hagerty

(57) ABSTRACT

A tampon applicator comprising a barrel having a generally tubular main body disposed intermediate an insertion end and a gripping end where the barrel is configured to contain a tampon capable of being expelled through the insertion end. A plunger having a generally tubular main body is partially disposed within the barrel for sliding movement and has a tampon engaging end within the barrel and a finger engaging end outside of the barrel. The gripping end of the barrel is formed with a reduced diameter region relative to the generally tubular main body located at the gripping end of the barrel and terminates in an outwardly and rearwardly graduated end through which the plunger extends. The finger engaging end of the plunger also has an outwardly and rearwardly graduated end which is configured to make contact with the outwardly flared end of the gripping end of the barrel to thereby limit sliding movement of the plunger. The plunger is configured so the outwardly and rearwardly graduated end will make contact with the outwardly and rearwardly graduated end at the gripping end of the barrel before the tampon engaging end can reach or contact the insertion end of the barrel.

18 Claims, 2 Drawing Sheets

NESTING TAMPON APPLICATOR

FIELD OF THE INVENTION

The present invention relates generally to tampon applicators having a barrel containing a tampon and a plunger disposed for sliding movement relative to the barrel for expelling the tampon and, more particularly, to a tampon applicator having a barrel with a gripping end and a plunger with a finger engaging end where the finger engaging end is configured to nest within the gripping end of the barrel.

BACKGROUND OF THE INVENTION

Tampon applicators are formed of both paperboard and plastic and they typically have a barrel and plunger used for expelling a tampon through an insertion end of the barrel into a vaginal cavity by applying a pressure to a finger engaging end of the plunger. Among the problems that have been noted is the fact that a portion, or all, of the applicator is out of the direct line of sight of a user during tampon insertion which can impair proper and comfortable delivery of the tampon. As a result, it is important that the tampon applicator incorporate suitable features making it possible to use the applicator for delivery of the tampon without any hindrance to gripping the barrel or controlling the plunger during tampon insertion.

In an effort to achieve these results, many different tampon applicators have been proposed having a wide variety of features. However, despite these efforts, there are still shortcomings which remain to be addressed. Generally, these shortcomings relate to the inability of known tampon applicators to fully and satisfactorily address the overall comfort of the user.

Among the shortcomings in existing tampon applicators is providing a secure, comfortable grip at the gripping end of the barrel. It is also recognized that the finger engaging ends of the plungers in existing tampon applicators often are found to be less than fully adequate for applying right amount of pressure to the plunger in a manner that ensures the proper and comfortable delivery of the tampon. Further, the barrel and plunger of existing tampon applicators have not always provided for stabilized relative sliding movement.

In addition, the insertion end of the barrel on many existing tampon applicators is formed to have a plurality of flexible petals defined by slits where the petals can open during tampon insertion and then close for withdrawal of the barrel. Thus, when pressure is applied to the finger engaging end of a plunger, the plunger engages the tampon and moves it forward in the barrel until the tampon engages the flexible petals, forcing them to open to thereby enable the tampon to be inserted into the vaginal cavity. However, if too much pressure is applied to the plunger by the user, it is possible for the plunger to be inserted too far into the barrel to the point that it can potentially prevent the flexible petals from fully closing after tampon insertion.

When the flexible petals are prevented from fully closing, it is possible for the petals to pinch the delicate tissue within the vaginal cavity, which can be very painful. Once this has occurred to a user of such tampon applicators, future use necessarily will be fraught with uncertainty and trepidation. Since the flexible petal design is otherwise highly functional, the possibility of over insertion of the plunger during insertion of the tampon is a serious detriment.

It would be desirable to have a tampon applicator having a secure, comfortable grip at the gripping end of the barrel, a plunger having a finger engaging end which is suitably configured for applying pressure in a manner that ensures the proper and comfortable delivery of a tampon from the barrel, and a construction providing for stabilized sliding movement of the plunger relative to the barrel while at the same time preventing over insertion of the plunger.

SUMMARY OF THE INVENTION

While it is known to provide a tampon applicator having a barrel containing a tampon and a plunger disposed for sliding movement relative to the barrel for expelling the tampon, it has remained to provide an applicator which overcomes the noted problems. Certain embodiments of the present disclosure provide a tampon applicator having improved features associated with both the barrel and the plunger. Such tampon applicators can not only provides a secure, comfortable grip at the gripping end of the barrel, but can also provide a plunger and barrel configured for stabilized relative sliding movement while preventing plunger over insertion.

In certain embodiments, the tampon applicator has a generally tubular main body disposed intermediate an insertion end and a gripping end. The barrel is configured to contain a tampon capable of being expelled through the insertion end. A plunger having a generally tubular main body is partially disposed within the barrel for sliding movement. The plunger has a tampon engaging end within the barrel and a finger engaging end outside of the barrel. The gripping end of the barrel is formed with a reduced diameter region relative to the generally tubular main body.

Specifically, the reduced diameter region at the gripping end of the barrel terminates in an outwardly and rearwardly graduated end through which the plunger extends. The finger engaging end of the plunger also has an outwardly and rearwardly graduated end configured to generally conform in shape to the outwardly and rearwardly graduated end of the gripping end of the barrel to limit sliding movement. The plunger is configured so the outwardly and rearwardly graduated ends of the plunger and the barrel will make contact before the tampon engaging end can reach the insertion end of the barrel. In one embodiment, a plurality of radially inwardly extending ribs in the reduced diameter region of the barrel define a guide for sliding movement of the plunger.

In certain embodiments, the insertion end of the barrel includes a plurality of flexible petals to enable the tampon to be expelled through the insertion end. Also, the tampon engaging end of the plunger may advantageously have a rim which extends outwardly of the generally tubular main body. By providing the rim on the tampon engaging end of the plunger, the rim can cooperate with the barrel to maintain the tampon engaging end of the plunger within the barrel.

In an exemplary embodiment, the outwardly and rearwardly graduated end at the gripping end of the barrel is a flared end and the outwardly and rearwardly graduated end at the finger engaging end of the plunger is also a flared end, and each of the outwardly flared ends is defined by a radius of curvature wherein the radius of curvature of the outwardly flared end at the finger engaging end of the plunger is less than or equal to the radius of curvature of the outwardly flared end at the gripping end of the barrel.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
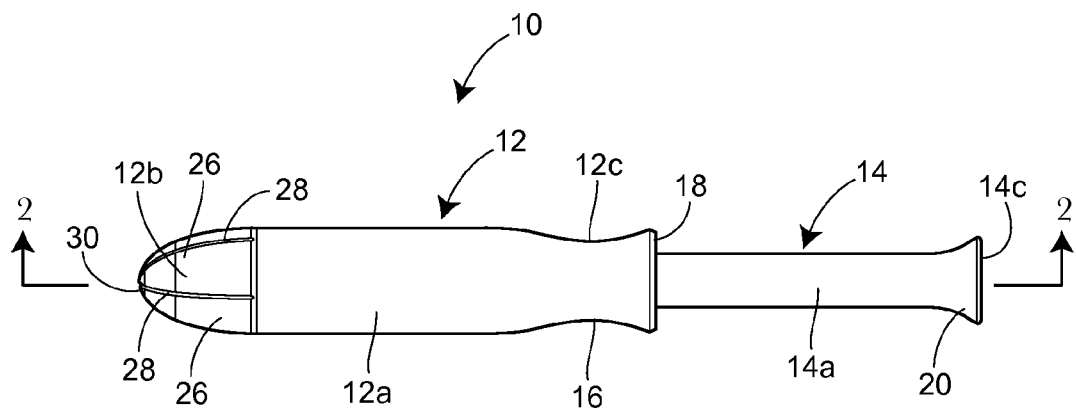
FIG. 1 is a side elevational view of a tampon applicator including a finger engaging end of a plunger configured to nest within a gripping end of a barrel.
Figure 2:
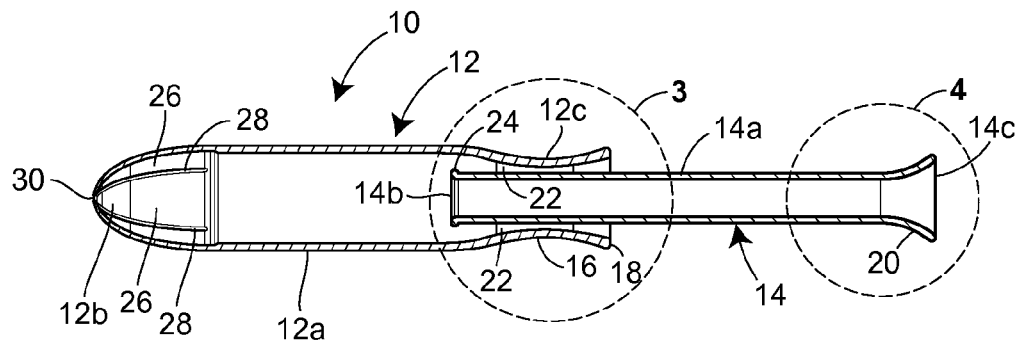
FIG. 2 is a cross-sectional view taken on the line 2-2 of FIG. 1 illustrating the plunger partially disposed within the barrel for relative sliding movement.

A tampon applicator 10 having a barrel 12 and a plunger 14 is illustrated in FIGS. 1 and 2 wherein the barrel 12 has a generally tubular main body 12a disposed intermediate an insertion end 12b and a gripping end 12c. The barrel 12 is configured to contain a tampon which can be expelled through the insertion end 12b. The plunger 14 has a generally tubular main body 14a partially disposed within the barrel 12. The plunger 14 has a tampon engaging end 14b within the barrel 12 and a finger engaging end 14c outside of the barrel 12. The gripping end 12c of the barrel 12 has a region 16 of reduced diameter relative to the generally tubular main body 12a, and it terminates in an outwardly and rearwardly graduated end 18 through which the plunger 14 extends.

Figure 5:
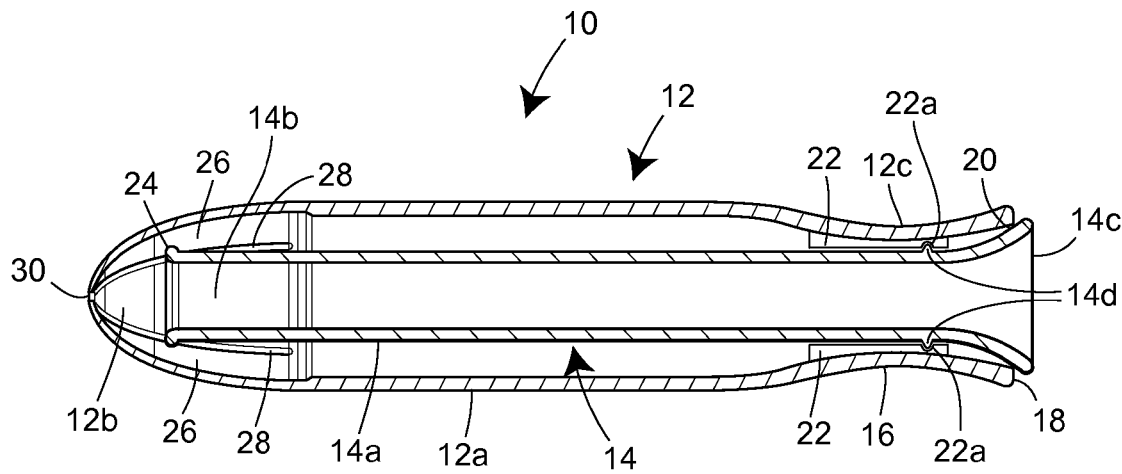
FIG. 5 is a cross-sectional view similar to FIG. 2 illustrating the position of the plunger after it has been used to insert a tampon into a vaginal cavity.

Referring to FIG. 2, the finger engaging end 14c of the plunger 14 also has an outwardly and rearwardly graduated end 20 which is configured to make contact with the outwardly and rearwardly graduated end 18 of the gripping end 12c of the barrel 12 to thereby limit the sliding movement of the plunger 14 within and relative to the barrel 12. Referring to FIG. 5, the plunger 14 is configured in size and shape relative to the barrel 12 so the outwardly and rearwardly graduated end 20 of the plunger 14 will make contact with the outwardly and rearwardly graduated end 18 of the barrel 12 before the tampon engaging end 14b of the plunger 14 can reach or contact the insertion end 12b of the barrel 12.

Referring to FIG. 2, in certain embodiments, the tampon applicator 10 includes a plurality of longitudinal ribs 22 within the barrel 12. The longitudinal ribs 22 extend radially inwardly and are located in the reduced diameter region 16 at the gripping end 12c of the barrel 12. The longitudinal ribs 22 serve to define a stabilizing guide for sliding movement of the plunger 14 relative to the barrel 12.

In certain embodiments, there are at least two opposed pairs of the radially inwardly extending longitudinal ribs 22 that can be equally spaced within the barrel 12 in the reduced diameter region 16 at the gripping end 12c of the barrel 12. Thus, and by way of example, there may suitably be four longitudinal ribs 22 equally spaced from one another by 90° about the inner circumferential surface of the barrel 12 in the reduced diameter region 16. However, there may be a greater number of longitudinal ribs 22, or as few as three longitudinal ribs 22, depending upon the degree of stabilization desired for the guided relative sliding movement of the plunger 14.

Figure 3:
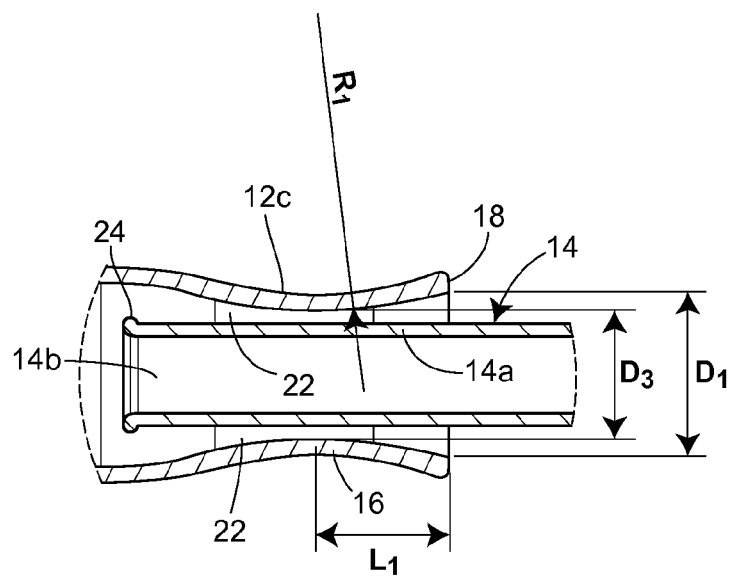
FIG. 3 is a cross-sectional detail view taken at "A" in FIG. 2 illustrating details of a gripping end of the barrel having radially inwardly extending ribs.

Referring to the cross-sectional detail view of FIG. 3, the tampon applicator 10 is illustrated as having two opposed pairs of the longitudinal ribs 22. The two radially inwardly extending longitudinal ribs 22 shown in FIG. 3 comprise a first opposed pair in which the ribs are separated by 180°, and it will be understood there can be a second opposed pair (not shown) in which the longitudinal ribs are also separated from each other by 180° and separated by 90° from the ribs of the first opposed pair. In certain embodiments, the diameter of the generally tubular main body 14a is about the same as the distance separating the longitudinal ribs 22 of each of the opposed pairs.

The tampon engaging end 14b of the plunger 14 can, in certain embodiments, include a rim 24 extending generally radially outwardly of the generally tubular main body 14a. The rim 24 can maintain the tampon engaging end 14b within the barrel 12. Specifically, the rim 24 can maintain the tampon engaging end 14b between the tampon and the radially inwardly extending longitudinal ribs 22.

Figure 4:
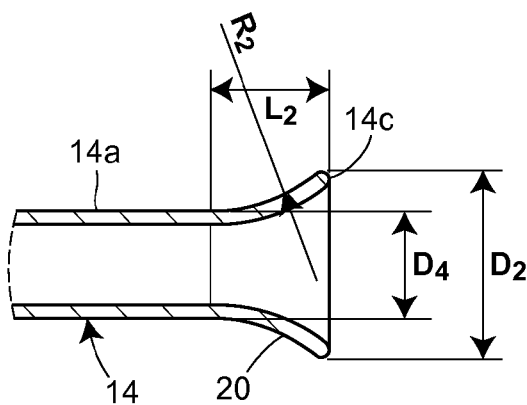
FIG. 4 is a cross-sectional detail view taken at "B" in FIG. 2 illustrating details of an outwardly flared end at a finger engaging end of the plunger.

Referring to FIGS. 3 and 4, the outwardly and rearwardly graduated end 18 at the gripping end 12c of the barrel 12 and the outwardly and rearwardly graduated end 20 at the finger engaging end 14c of the plunger 14 each are flared ends, and the outwardly flared ends 18 and 20 each are defined by a radius of curvature $R_1$ and $R_2$, respectively. The length $L_1$ of the reduced diameter region 16 and the radius of curvature $R_1$ of the outwardly flared end 18 are selected to provide a secure, comfortable grip. By way of example, the radius of curvature $R_1$ may be approximately 20.61 mm and the length $L_1$ from the outwardly flared end 18 to the narrowest point in the reduced diameter region 16 may be approximately 9.23 mm.

With regard to the foregoing, the term "outwardly and rearwardly graduated end 18" has reference to the fact the end 18 increases in size relative to the gripping area 12c of the barrel 12 in a direction away from the insertion end 12b. Likewise, the term "outwardly and rearwardly graduated end 20" has reference to the fact the end 20 increases in size relative to the generally tubular main body 14a of the plunger 14 in a direction away from the tampon engaging end 14b. In certain embodiments, the outwardly and rearwardly graduated ends 18 and 20 are each defined by a radius of curvature $R_1$ and $R_2$ so as to be flared as shown in FIGS. 3 and 4 and to nest as shown in FIG. 5, although in other embodiments it is sufficient for the ends 18 and 20 to take other shapes or forms as long as they are similarly configured and increase in size.

Also, by way of example, the radius of curvature $R_2$ of the outwardly flared end 20 at the finger engaging end 14c of the plunger 14 may be approximately 12.10 mm, and the length $L_2$ from the outwardly flared end 20 to the constant diameter generally tubular main body 14a of the plunger 14 may be approximately 7.16 mm. Also, by way of example, for an easy to hold applicator the inner diameter $D_1$ at the outwardly flared end 18 at the gripping end 12c of the barrel 12 may be approximately 11.46 mm whereas the outer diameter $D_2$ of the outwardly flared end 20 of the finger engaging end 14c of the plunger 14 may be approximately 10.96 mm to accommodate nesting of the outwardly flared ends 18 and 20.

Further, by way of example, the radius of curvature $R_2$ of the outer surface of the outwardly flared end 20 at the finger engaging end 14c of the plunger 14 can be within a range of anywhere from 50% smaller to 50% larger than the radius of curvature $R_1$ of the inner surface of the outwardly flared end 18 of the gripping end 12c of the barrel 12.

While in the foregoing example, the radius of curvature $R_2$ of the outwardly flared end 20 at the fingering engaging end 14c of the plunger 14 is less than the radius of curvature $R_1$ of the outwardly flared end 18 at the gripping end 12c of the barrel 12, it is believed that adequate nesting of the outwardly flared end 20 within the outwardly flared end 18 will be achieved so long as the radius of curvature $R_2$ is equal to or less than the radius of curvature $R_1$.

In certain embodiments, it is believed that adequate nesting of the outwardly flared end 20 within the outwardly flared end 18 will be achieved if the outer diameter $D_2$ of the outwardly flared end 20 is no greater than the inner diameter $D_1$ at the outwardly flared end 18 of the gripping end 12c of the barrel 12. In one embodiment, adequate nesting is achieved with the outer diameter $D_2$ of the outwardly flared end 20 (which includes the thickness of the finger engaging end 14c) approximately equal to or less than the inner diameter $D_1$ at the outwardly flared end 12c of the barrel 12 but at least as great as the minimum diameter $D_3$ in the reduced diameter region 16 of the barrel 12. With these relationships, there will be a desirable tactile indication of when to cease applying pressure to the finger engaging end 14c of the plunger 14 by reason of the finger on the finger engaging end 14a of the plunger 14 making contact with the outwardly flared end 18 at the gripping end 12c of the barrel 12.

Figure 6:
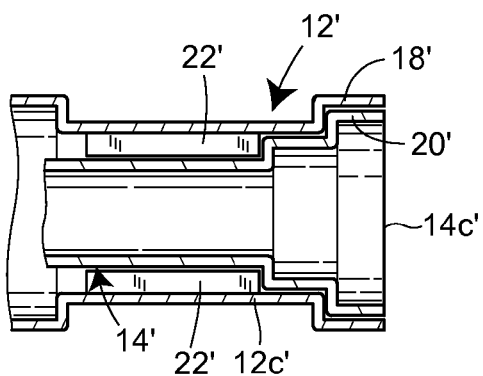
FIG. 6 is a cross-sectional view of an alternative embodiment of a finger engaging end of a plunger configured to nest within a gripping end of a barrel.

Referring to another embodiment illustrated in FIG. 6, the barrel 12' has an outwardly and rearwardly graduated end 18' at the gripping end 12c' of the barrel 12' and the plunger 14' has an outwardly and rearwardly graduated end 20' at the finger engaging end 14c' of the plunger 14'. However, the outwardly and rearwardly graduated ends 18' and 20' do not comprise outwardly flared ends each defined by a radius of curvature but, rather, they are defined by stepped surfaces. Thus, the outwardly and rearwardly graduated ends 18' and 20' of the barrel 12' and the plunger 14' are formed as stepped arrangements with the stepped end 20' configured to nest within the stepped end 18' after a tampon has been expelled from the barrel 12'.

In certain other embodiments, the shape of the ends of the barrel and plunger can take still other forms provided only that they are outwardly and rearwardly graduated and the end of the plunger will nest within the end of the barrel after a tampon has been expelled from the barrel.

Referring to FIG. 3, the ribs 22 preferably do not extend to the outwardly flared end 18 at the gripping end 12c of the barrel 12 but, instead, are recessed so the outwardly flared end 20 can nest deeply within the outwardly flared end 18. While the ribs 22 need not be recessed, doing so accommodates the deep nesting which makes it possible to achieve the desirable tactile indication of when to cease applying finger pressure to the finger engaging end 14c of the plunger 14.

Referring to FIG. 5, each of the longitudinal ribs 22 may be provided with an annular recess 22a near or adjacent to the ends of the ribs 22 located nearest the outwardly flared end 18 of the barrel 12. The plunger 14 may then include a circumferential enlargement or collar 14d positioned so that it will snap into the annular recesses 22a just as the outwardly flared end 20 of the plunger 14 makes contact with the outwardly flared end 18 of the barrel 12. As a result, the plunger 14 will be held and restrained against movement substantially entirely within the barrel 12 for disposal with the barrel 12 after the plunger 14 has been used for inserting a tampon.

In certain embodiments utilizing the annular recess 22a in each of the longitudinal ribs 22 and the circumferential enlargement or collar 14d on the plunger 14, there will be slight resistance, and then an audible click, as the circumferential enlargement or collar 14d first contacts the ends of the longitudinal ribs 22 and then snaps into the annular recesses 22a to thereby provide both an audible indication as well as an additional tactile indication of when to cease applying finger pressure to the finger engaging end 14c of the plunger 14.

As illustrated in FIG. 3, in certain embodiments, the shape of substantially the entire reduced diameter region 16 at the gripping end 12c of the barrel 12 can be defined by the radius of curvature $R_1$ such that the minimum diameter $D_3$ in the reduced diameter region 16 may be approximately 8.91 mm.

Further, by way of example, in certain embodiments, the diameter $D_4$ of the generally tubular main body 14a of the plunger 14 which, as noted above, may be approximately the same as the distance separating the longitudinal ribs 22 of each of the opposed pairs of ribs, may be approximately 7.44 mm.

In the foregoing example, the radius of curvature $R_2$ of the outwardly flared end 20 at the finger engaging end 14c of the plunger 14 results in an outer diameter $D_2$ that is entirely well suited for applying finger pressure to the plunger 14 in a manner that ensures the proper and comfortable delivery of the tampon, while the diameter $D_4$ of the generally tubular main body 14a of the plunger 14 and the distance separating the longitudinal ribs 22 of each of the opposed pair of ribs result in a barrel 12 and a plunger 14 that provide for stabilized sliding movement of the plunger 14 relative to the barrel 12 during tampon insertion.

Referring to FIGS. 1 and 2, the insertion end 12b of the barrel 12 will be seen to have a plurality of flexible petals 26. The flexible petals 26 normally define a generally dome shaped contour for the insertion end 12b of the barrel 12 which is a suitable shape to facilitate comfortable insertion of the barrel 12 into the vaginal cavity. In certain embodiments, the flexible petals 26 can be defined by a plurality of slits 28 that extend from the tip 30 to the generally tubular main body 12a.

In certain embodiments, by forming the flexible petals 26 of a thin-walled plastic material, the slits 28 can permit the flexible petals 26 to easily open in response to movement of the tampon when pressure is applied to the finger engaging end 14c of the plunger 14. After the tampon has been inserted into the vaginal cavity, the flexible petals 26 are shape recoverable and therefore close to return to their normal generally dome shaped contour. In addition, the plunger 14 won't interfere with the flexible petals 26 closing because the outwardly flared end 20 will nest within the outwardly flared end 18 before the tampon engaging end 14b can reach the insertion end 12b of the barrel 12.

As will be appreciated from FIG. 5, the rim 24 on the tampon engaging end 14b of the plunger 14 will still be spaced from the inner surface of the closed flexible petals 26 when the outwardly flared end 20 is fully nested within the outwardly flared end 18 and, therefore, the insertion end 12b of the barrel 12 can return to its normal generally dome shaped contour with the flexible petals 26 closed so there is little or no possibility for the flexible petals 26 to be able pinch the delicate tissue within the vaginal cavity during withdrawal of the barrel 12.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon applicator, comprising:
    a barrel having a generally tubular main body disposed intermediate an insertion end and a gripping end, the barrel being configured to contain a tampon capable of being expelled through the insertion end;
    a plunger having a generally tubular main body partially disposed within the barrel for sliding movement, the plunger having a tampon engaging end within the barrel and a finger engaging end outside of the barrel;
    the gripping end of the barrel having a reduced diameter region relative to the generally tubular main body, the reduced diameter region terminating in an outwardly and rearwardly graduated end through which the plunger extends;
    a plurality of radially inwardly extending longitudinal ribs within the barrel in the reduced diameter region;
    the finger engaging end of the plunger also having an outwardly and rearwardly graduated end configured to generally conform in shape to the outwardly and rearwardly graduated end of the gripping end of the barrel to thereby limit sliding movement of the plunger;
    the plunger being configured so the outwardly and rearwardly graduated end will make contact with, the outwardly and rearwardly graduated end at the gripping end of the barrel before the tampon engaging end can reach the insertion end of the barrel.

2. The tampon applicator of claim 1 wherein the insertion end of the barrel includes a plurality of flexible petals defined by a plurality of slits to enable the tampon to be expelled through the insertion end.

3. The tampon applicator of claim 1 wherein the tampon engaging end of the plunger has a rim extending outwardly of the generally tubular main body for maintaining the tampon engaging end within the barrel.

4. The tampon applicator of claim 1 wherein the outwardly and rearwardly graduated end at the gripping end of the barrel and the outwardly and rearwardly graduated end at the finger engaging end of the plunger each are flared ends and defined by a radius of curvature.

5. The tampon applicator of claim 4 wherein the radius of curvature of the outwardly flared end at the finger engaging end of the plunger is less than the radius of curvature of the outwardly flared end at the gripping end of the barrel.

6. The tampon applicator of claim 4 wherein the radius of curvature of the outwardly flared end at the finger engaging end of the plunger is equal to the radius of curvature of the outwardly flared end at the gripping end of the barrel.

7. The tampon applicator of claim 1 wherein the radially inwardly extending longitudinal ribs do not extend all the way to the outwardly flared and rearwardly graduated end of the gripping end.

8. The tampon applicator of claim 1 wherein each of the a plurality of radially inwardly extending longitudinal ribs comprises an annular recess, and wherein the plunger comprises a circumferential enlargement or collar proximate the finger engaging end that is capable of at least partially fitting into the annular recesses.

9. A tampon applicator, comprising:
    a barrel having a generally tubular main body disposed intermediate an insertion end and a gripping end, the barrel being configured to contain a tampon capable of being expelled through the insertion end;
    a plunger having a generally tubular main body partially disposed within the barrel for sliding movement, the plunger having a tampon engaging end within the barrel and a finger engaging end outside of the barrel;
    the gripping end of the barrel having a reduced diameter region relative to the generally tubular main body, the reduced diameter region terminating in an outwardly flared end through which the plunger extends;
    a plurality of radially inwardly extending longitudinal ribs within the barrel in the reduced diameter region at the gripping end of the barrel to define a stabilizing guide for sliding movement of the plunger;
    the finger engaging end of the plunger also having an outwardly flared end configured to nest within the outwardly flared end of the gripping end of the barrel to thereby limit sliding movement of the plunger;
    the plunger being configured so the outwardly flared end will nest within the outwardly flared end at the gripping end of the barrel before the tampon engaging end can reach the insertion end of the barrel;
    the tampon engaging end of the plunger including a rim extending outwardly of the generally tubular main body of the plunger for maintaining the tampon engaging end between the tampon and the radially inwardly extending longitudinal ribs in the reduced diameter region of the barrel.

10. The tampon applicator of claim 9 wherein the insertion end of the barrel includes a plurality of flexible petals defined by a plurality of slits to enable the tampon to be expelled through the insertion end.

11. The tampon applicator of claim 9 wherein the outwardly flared end at the gripping end of the barrel and the outwardly flared end at the finger engaging end of the plunger each are defined by a radius of curvature.

12. The tampon applicator of claim 11 wherein the radius of curvature of the outwardly flared end at the finger engaging end of the plunger is less than the radius of curvature of the outwardly flared end at the gripping end of the barrel.

13. The tampon applicator of claim 11 wherein the radius of curvature of the outwardly flared end at the finger engaging end of the plunger is equal to the radius of curvature of the outwardly flared end at the gripping end of the barrel.

14. A tampon applicator, comprising:
    a barrel having a generally tubular main body disposed intermediate an insertion end and a gripping end, the barrel being configured to contain a tampon capable of being expelled through the insertion end;
    a plunger having a generally tubular main body partially disposed within the barrel for sliding movement, the plunger having a tampon engaging end within the barrel and a finger engaging end outside of the barrel; and
    the gripping end of the barrel having a reduced diameter region relative to the generally tubular main body, the reduced diameter region terminating in a grip end through which the plunger extends; and
    a plurality of radially inwardly extending longitudinal ribs within the barrel in the reduced diameter region;

wherein the finger engaging end of the plunger has a maximum outer diameter that is the same size or smaller than an inner diameter of the grip end.

15. The tampon applicator of claim 14 wherein the plurality of radially inwardly extending longitudinal ribs includes at least two opposed pairs.

16. The tampon applicator of claim 14 wherein the maximum outer diameter of the finger engaging end of the plunger is smaller than the inner diameter of the grip end.

17. The tampon applicator of claim 14 wherein each of the a plurality of radially inwardly extending longitudinal ribs comprises an annular recess, and wherein the plunger comprises a circumferential enlargement or collar proximate the finger engaging end that is capable of at least partially fitting into the annular recesses.

18. The tampon applicator of claim 14 wherein the radially inwardly extending longitudinal ribs do not extend all the way to the grip end.

\* \* \* \* \*